US012253662B2

United States Patent
Bartels et al.

(10) Patent No.: US 12,253,662 B2
(45) Date of Patent: Mar. 18, 2025

(54) PHASE-SENSITIVE SINGLE MOLECULE LOCALIZATION MICROSCOPY

(71) Applicant: Colorado State University Research Foundation, Fort Collins, CO (US)

(72) Inventors: Randy A. Bartels, Fort Collins, CO (US); Jeffrey J. Field, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 590 days.

(21) Appl. No.: 17/648,923

(22) Filed: Jan. 25, 2022

(65) Prior Publication Data

US 2022/0236549 A1 Jul. 28, 2022

Related U.S. Application Data

(60) Provisional application No. 63/141,166, filed on Jan. 25, 2021.

(51) Int. Cl.
  *G01N 21/64*   (2006.01)
  *G02B 21/00*   (2006.01)
  *G01N 33/58*   (2006.01)

(52) U.S. Cl.
  CPC ..... *G02B 21/0056* (2013.01); *G01N 21/6458* (2013.01); *G02B 21/0076* (2013.01); *G01N 33/58* (2013.01)

(58) Field of Classification Search
  CPC ............ G02B 21/0056; G02B 21/0076; G02B 21/06; G02B 21/367; G02B 27/58; G02B 21/16; G01N 21/6458; G01N 33/58
  See application file for complete search history.

(56) References Cited

U.S. PATENT DOCUMENTS

| | | |
|---|---|---|
| 7,483,635 B2 | 1/2009 | Xu |
| 8,553,337 B2 | 10/2013 | Webb et al. |
| 8,554,035 B2 | 10/2013 | Xu et al. |
| 8,705,184 B2 | 4/2014 | Xu et al. |
| 10,073,025 B2 | 9/2018 | Bartels et al. |

(Continued)

FOREIGN PATENT DOCUMENTS

| | | |
|---|---|---|
| WO | 2006093962 A2 | 9/2006 |
| WO | 2006102074 A2 | 9/2006 |

(Continued)

*Primary Examiner* — Dani Fox
*Assistant Examiner* — Mamadou Faye
(74) *Attorney, Agent, or Firm* — MASCHOFF BRENNAN; Paul G. Johnson

(57) ABSTRACT

In an embodiment, a method includes obtaining radiation emitted from a radiation source. The method includes modulating the radiation with a time-varying modulation to generate a time-varying illumination pattern with a known modulation. The illumination pattern includes a time-varying intensity for each of a plurality of spatial locations. The method includes illuminating a target volume with the illumination pattern. The method includes collecting a signal generated by one or more objects within the target volume in response to illumination by the illumination pattern. The method includes estimating a location of each of the one or more objects based on the collected signal and the known modulation.

17 Claims, 6 Drawing Sheets

(56) References Cited

U.S. PATENT DOCUMENTS

| | | | |
|---|---|---|---|
| 2013/0128042 A1* | 5/2013 | Bridge | H04N 25/00 |
| | | | 348/143 |
| 2013/0324858 A1 | 12/2013 | Xu et al. | |
| 2014/0087971 A1* | 3/2014 | Kiesel | G01N 21/6452 |
| | | | 506/30 |
| 2018/0303573 A1* | 10/2018 | Trulson | G02B 21/16 |
| 2020/0069233 A1 | 3/2020 | Xu et al. | |

FOREIGN PATENT DOCUMENTS

| | | |
|---|---|---|
| WO | 2008094274 A1 | 8/2008 |
| WO | 2011091340 A1 | 7/2011 |
| WO | 2012134427 A2 | 10/2012 |
| WO | 2018222727 A1 | 12/2018 |

\* cited by examiner

PHASE-SENSITIVE SINGLE MOLECULE LOCALIZATION MICROSCOPY

CROSS-REFERENCE TO RELATED APPLICATION

This application claims the benefit of and priority to U.S. Provisional App. No. 63/141,166 filed Jan. 25, 2021. The 63/141,166 provisional application is incorporated herein by reference.

FIELD

The present disclosure generally relates to phase-sensitive single molecule localization microscopy.

BACKGROUND

Unless otherwise indicated herein, the materials described herein are not prior art to the claims in the present application and are not admitted to be prior art by inclusion in this section.

Imaging molecular compounds may be facilitated by fluorescence microscopy in which radiation is directed towards a compound of interest, and light emitted by the compound of interest in response to absorbing the radiation, called fluorescent emissions, is observed. Fluorescence microscopy may be helpful for imaging biochemical compounds for applications such as basic research to clinical diagnoses. Some biochemical compounds may exhibit unique fluorescent emissions such that the biochemical compounds may be identified based on their fluorescent behavior.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

SUMMARY

In an example embodiment, a method includes obtaining radiation emitted from a radiation source. The method includes modulating the radiation with a time-varying modulation to generate a time-varying illumination pattern with a known modulation. The illumination pattern includes a time-varying intensity for each of a plurality of spatial locations. The method includes illuminating a target volume with the illumination pattern. The method includes collecting a signal generated by one or more objects within the target volume in response to illumination by the illumination pattern. The method includes estimating a location of each of the one or more objects based on the collected signal and the known modulation.

In another example embodiment, a microscopy system includes a radiation source, one or more modulation masks, a sample, one or more photodetectors, and a computing system. The radiation source is configured to emit radiation. The modulation mask is positioned to receive radiation from the radiation source and is configured to modulate the radiation with a time-varying modulation to generate a time-varying illumination pattern with a known modulation. The illumination pattern includes a time-varying intensity for each of a plurality of spatial locations. The sample includes one or more objects in a target volume, such as on a sample slide, and is positioned to receive the time-varying illumination pattern. The photodetector(s) are positioned and configured to collect a signal generated by the objects within the target volume in response to illumination by the illumination pattern. The computing system is coupled to the photodetector(s) and is configured to estimate a location of each of the objects based on the collected signal and the known modulation.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

Example embodiments will be described and explained with additional specificity and detail through the accompanying drawings in which.

DETAILED DESCRIPTION

Figure 1:
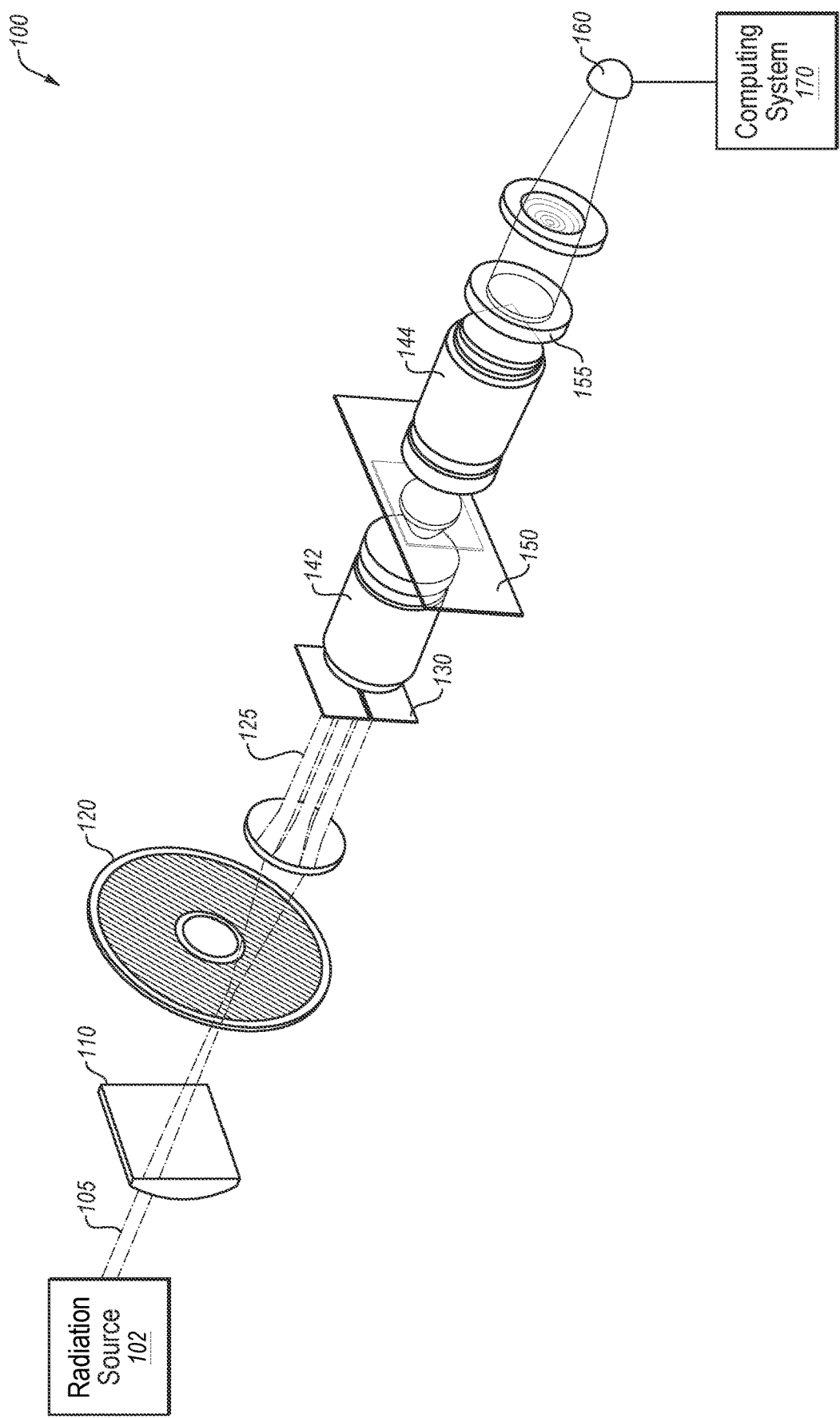
FIG. 1 is a diagram of an example embodiment of a microscope configured for three-dimensional imaging and localization of optically interactive objects using a large quasi-plane wave illumination according to at least one embodiment of the present disclosure.

Existing optical imaging techniques may be capable of resolving spatial features of a sample being imaged. The resolutions achievable by these existing optical imaging techniques may be limited by light diffraction wavelengths, which are defined by the optical wavelength of light in the transverse direction of light propagation. As such, existing optical imaging techniques may resolve spatial features at a spatial resolution limit of approximately 300 nanometers (nm).

Super-resolution imaging processes may exceed the light diffraction limits of the above-described existing optical imaging techniques using techniques such as multiplexing spatial-frequency bands, probing near-field electromagnetic disturbances, and/or encoding spatial-frequency details using multiple polarization states. Some examples of super-resolution imaging processes may include photoactivated localization microscopy, stochastic optical reconstruction microscopy, stimulated emission depletion microscopy, and structured illumination microscopy. By exceeding the light diffraction limits, super-resolution imaging processes may facilitate research into new mechanisms of signaling pathways and biochemical interactions cells and/or organisms. However, existing super-resolution imaging processes are currently limited in terms of their abilities to provide super-resolution imaging in an axial direction (i.e., the direction in which light is propagating). Such super-resolution imaging processes typically fail to accurately image tissues and other three-dimensional cell cultures because of strong optical scattering, specimen aberrations, limited imaging volumes, and/or other optical limitations.

The present disclosure relates to, among other things, a super-resolution imaging approach that facilitates use of super-resolution imaging in three-dimensional cell cultures and other complex biological environments. A microscope may use time-varying illumination patterns and single-pixel detection methods (e.g., using a photodetector) to improve the spatial imaging resolution of sample objects, such as fluorescent molecules. Additionally or alternatively, absorption spectra, linear scattering, and/or non-linear optical scattering associated with the sample objects based on the time-varying illumination patterns may be used to improve spatial imaging resolution of the sample objects. Additionally or alternatively, encoding phase information and implementing a single-pixel detection strategy as described in the present disclosure may reduce the effects of optical aberrations and optical scattering on imaging the sample objects.

Using a super-resolution imaging approach as described in the present disclosure may improve spatial and temporal visualization of interactions between small groups of molecular compounds to a scale of approximately 25 to 50 nm and tens of seconds (or even shorter), respectively. For example, mitotic cell division may be imaged at greater spatial and temporal resolutions such that more insight into a wide range of health ailments may be made. More specifically, how kinetochores of mitotic chromosomes attach to spindle microtubules and how these attachments are regulated to prevent chromosome segregation errors and aneuploidy could improve understanding of birth defects and human cancers. As another example, the super-resolution imaging approach of the present disclosure may improve understanding of disease processes by determining how proteins generate attachment sites for spindle microtubules, how the attachment strength to the microtubules is regulated, and/or how the attachment status is relayed to a spindle assembly checkpoint.

Reference will now be made to the drawings to describe various aspects of example embodiments of the invention. It is to be understood that the drawings are diagrammatic and schematic representations of such example embodiments, and are not limiting of the present invention, nor are they necessarily drawn to scale.

FIG. 1 is a diagram of an example embodiment of a microscopy system 100 configured for three-dimensional imaging and/or localization of one or more sample objects using large quasi-plane wave illumination according to at least one embodiment of the present disclosure. In some embodiments, the microscopy system 100 may use a single molecule localization microscopy (SMLM) approach in which sparse groups of individual fluorophores relating to a sample object included in a target volume are activated by directing radiation towards the fluorophores. Centroids of point-spread functions for each fluorophore may be collected (e.g., by a photodetector), and the centroids may be used to construct an image with a random distribution of excited fluorophores to represent the sample object.

The microscopy system 100 may include or be coupled to a radiation source 102 that emits radiation 105 and a lens 110 of a microscope that may direct the emitted radiation 105 towards one or more modulation masks 120 and/or focus or otherwise reshape the emitted radiation 105. For example, the lens 110 may focus the emitted radiation 105 on the modulation mask(s) 120 In some embodiments, the radiation 105 may be emitted as a single beam, multiple discrete pulses, or as multiple beams of radiation. In these and other embodiments, the radiation 105 may include electromagnetic waves of various wavelengths, such as infrared radiation, visible light, and/or ultraviolet radiation. For example, the radiation source 102 may include an ytterbium fiber laser oscillator that may produce electromagnetic radiation in ultrashort pulses (e.g., 30 femtosecond (fs) pulses) centered at a particular wavelength (e.g., 1060 nm). Additionally or alternatively, the radiation 105 may include high spatial coherence such that the radiation 105 has highly correlated relationships at different points in space along the electromagnetic waves. In some embodiments, a modal decomposition of radiation with high spatial coherence may contain more than twenty-five coherent modes.

In some embodiments, the lens 110 may include a cylindrical or a convex shape to focus the radiation 105 such that the radiation 105 is aimed at a particular area on the modulation mask(s) 120. Additionally or alternatively, the lens 110 may be configured to generate one or more beams of radiation based on the radiation 105. For example, the radiation 105 aimed at the lens 110 may include a single beam of radiation, and the lens 110 may split the single beam of radiation into two or more beams. Each radiation beam of the multiple beams of radiation directed from the lens 110 towards the modulation mask(s) 120 may include a respective phase, and two or more of the radiation beams may include different phases such that a spatial phase difference exists between the two or more radiation beams. The spatial phase difference between the two or more radiation beams may be encoded into temporal oscillations associated with emitted fluorescence by fluorophores towards which the radiation beams are directed such that spatial phase disruptions occurring during the imaging process, including sample and microscope aberrations, may be isolated and removed during post-processing. In these and other embodiments, the lens 110 may include a single lens as illustrated in FIG. 1, or the lens 110 may refer to multiple lenses configured to operate together or separately to focus, redirect, and/or split the radiation 105.

The modulation mask(s) 120 may receive the radiation 105 from the lens 110 and generate a time-varying illumination pattern 125. The illumination pattern 125 formed after the radiation 105 passes through the modulation mask(s) 120 may be generated based on a modulation pattern printed, etched, or otherwise formed on or by the modulation mask(s) 120. The modulation mask(s) 120 may generally include a spatial light modulator (SLM), such as a generally circular (or other shape) amplitude transmission grating with varying groove density as a function of angle, a phase mask, a micro-electro-mechanical-system (MEMS) SLM, a digital light processing (DLP) SLM, a liquid display (LCD) SLM, a phase-only liquid crystal on silicon (LCOS) SLM, two or more deformable mirrors, ferroelectric liquid crystal modulators, or any other system or device that can impart a change in amplitude and/or phase of the radiation

105 in the modulation plane. Because the modulation pattern on the modulation mask(s) 120 is known and the illumination pattern 125 is formed in relation to the known modulation pattern, the illumination pattern 125 may include known time-varying illumination intensities at various spatial locations in a target volume of a sample 150. In some embodiments, the modulation pattern on the modulation mask(s) 120 may be formed as an amplitude transmission grating with a varying groove density as a function of angle. Each radial position on the modulation mask 120 may include changing on-off intensity modulation such that each transverse spatial position on the modulation mask(s) 120 may be tagged with a modulation frequency different from the modulation frequencies tagged at each other transverse spatial position. In at least one embodiment, for example, the modulation mask(s) 120 may include a maximal density of seventy lines per millimeter with an overall magnification of 77 and a numerical aperture (NA) of 1.05.

Additionally or alternatively, the illumination pattern 125 may extend over a volume greater than a depth of field (DOF) of camera-based imaging techniques. The illumination pattern 125 may include different features at one or more points in the target volume on the sample 150 such that intensity and phase information may be jointly used to determine locations of isolated fluorescent emitters using a single-element photodetector 160. In some embodiments, the time-varying intensity of the illumination pattern 125 may be determined according to the following relationship:

$$I(x,y,z,t) \propto I_0(x,y,z,t) + I_1(x,y,z,t)\cos[\Delta_\phi(x,y,z,t)] \quad (1)$$

in which a background intensity, $I_0(x, y, z, t)$, and a product of an envelope of illumination intensity that determines a DOF and/or an imaging volume, $I_1(x, y, z, t)$, and the cosine of the spatial phase difference, $\Delta\phi(x, y, z; t)$ are summed to determine the time-varying intensity of the illumination pattern 125. In Equation (1), x, y, and z are three-dimensional coordinates and t is time.

In some embodiments, the illumination pattern 125 may be scanned through one or more spatial filters 130 such that a range of spatial frequencies narrower than a numerical aperture of the radiation 105 is obtained to block a diffracted order and break axial symmetry. Alternatively or additionally, the optics and illumination pattern 125 of the microscopy system 100 may obtain a range of spatial frequencies narrower than the numerical aperture of the radiation 105 to block a diffracted order and break axial symmetry. The numerical aperture may represent an entire range of spatial frequencies of the radiation 105, and scanning any of the spatial frequencies included in the numerical aperture at any time t may increase a DOF of the illumination pattern 125. In these and other embodiments, spatial frequencies along the entirety of the numerical aperture may be serially scanned through the spatial filter(s) 130 over a period of time by adjusting the radiation 105 passing through the lens 110, the illumination pattern 125 passing through the modulation mask 120, a position or orientation of the spatial filter(s) 130, or some combination thereof.

Figure 2:
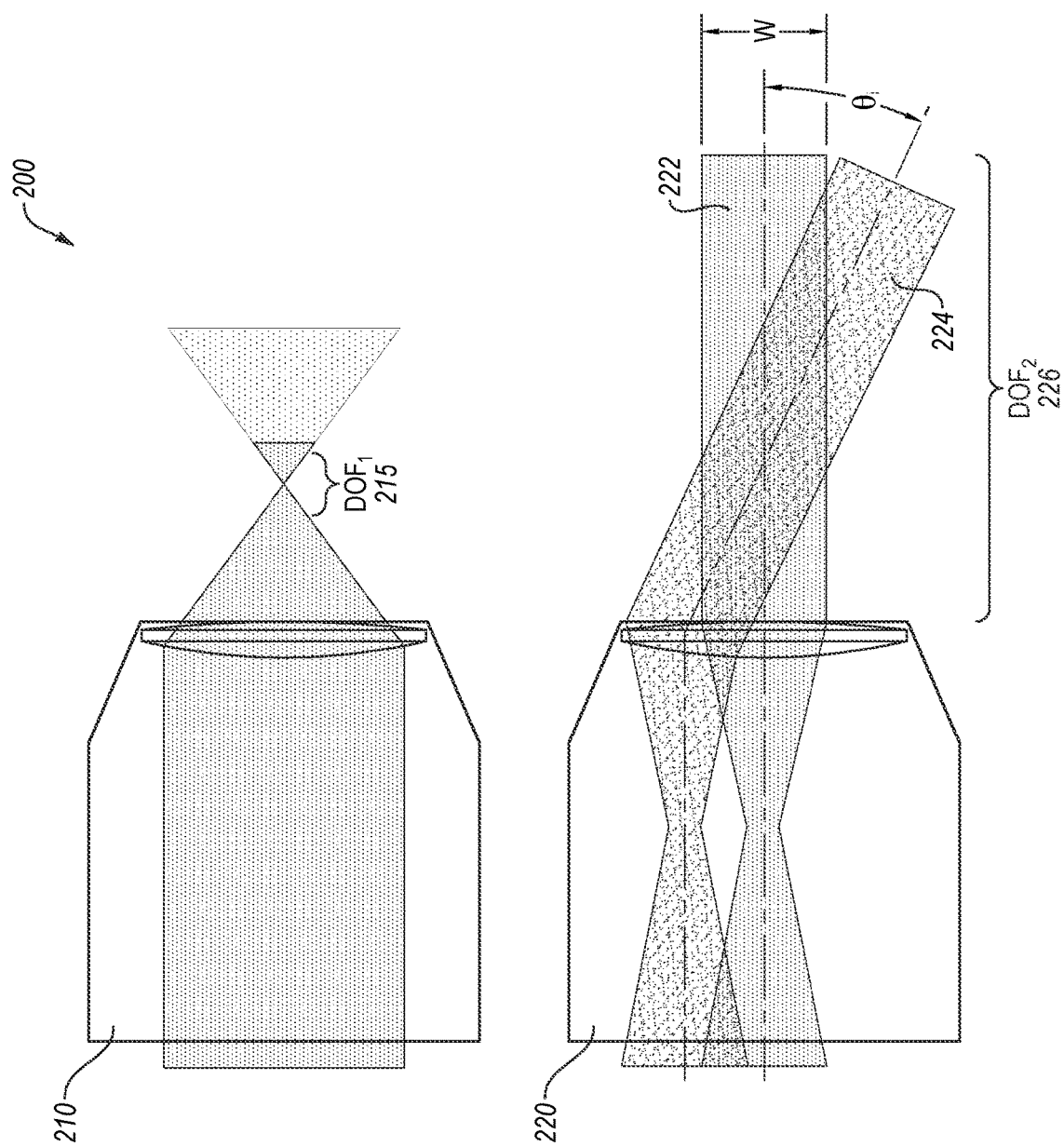
FIG. 2 illustrates a depth of field (DOF) comparison of the DOF generated via a tight focus process and the large quasi-plane wave illumination process according to at least one embodiment of the present disclosure.

FIG. 2 illustrates a DOF comparison 200 of a first $DOF_1$ 215 generated via a tight focus process 210 and a second $DOF_2$ 226 generated via a partial pupil illumination process 220 at a particular point in time according to at least one embodiment of the present disclosure. The first $DOF_1$ 215 is an example of a tightly focused DOF formed using the tight focus process 210 associated with existing SMLM techniques. The tight focus process 210 may include affecting coherent interference between various illumination beams over a broad range of spatial frequencies. Because the illumination beams are projected at a broad range of spatial frequencies, some of the illumination beams at the highest spatial frequencies may propagate at extreme angles relative to an optic axis. As such, the first $DOF_1$ 215 is generated at a tight focal spot in which all of the spatial frequencies spatially overlap in a small axial range represented by the first $DOF_1$ 215.

In some embodiments, the second $DOF_2$ 226 may be generated via the partial pupil illumination process 220 as described in relation to one or more embodiments of the present disclosure. The second $DOF_2$ 226 may be determined based on an intersection between a first illumination beam 222 and one or more second illumination beams 224. The first illumination beam 222 and the second illumination beam 224 may have a phase difference between the two or more illumination beams because the two or more illumination beams may cross at an angle, $\theta_i$, relative to one another such that the first illumination beam 222 and the other illumination beams 224 are not parallel to each other.

In these and other embodiments, a size of the first $DOF_1$ 215 and/or the second $DOF_2$ 226 may be determined based on the following equations:

$$\Delta f_x = \frac{2NA}{\lambda} \quad (2)$$

$$\delta f_x = \frac{\Delta f_x}{N} \quad (3)$$

in which $\delta f_x$ is a differential of spatial frequency in a small pupil plane resulting from spatial frequency excitation, $\Delta f_x$ is the change in spatial frequency across the pupil plane, NA is a numerical aperture, $\lambda$ is a wavelength of radiation illuminating the pupil plane, and N is a large integer, such as 1,000).

Assuming a Gaussian model, a spatial frequency distribution may be approximated as:

$$e^{-\left(\frac{f_x}{\delta f_x}\right)^2} - e^{-(\pi w_0 f_x)^2} \quad (4)$$

in which $w_0$ is approximated as:

$$w_0 \approx \frac{1}{\pi \delta f_x} \quad (5)$$

such that a spatial Gaussian intensity is proportional to:

$$e^{-2\left(\frac{P}{w(z)}\right)^2} \quad (6)$$

in which:

$$w(z) = w_0 \sqrt{1 + \left(\frac{Z}{Z_R}\right)^2} \quad (7)$$

Based on Equations (2)-(7), the DOF may be computed according to the following equations:

$$Z_R = \frac{\pi w_0^2}{\lambda} = \frac{\pi}{\lambda}\left(\frac{1}{\pi \delta f_x}\right)^2 = \frac{1}{\pi \lambda}\left(\frac{N}{\Delta f_x}\right)^2 = \frac{1}{\delta \pi}\left(\frac{\lambda N}{NA}\right)^2 = \frac{\lambda}{4\pi}\left(\frac{N}{NA}\right)^2 \quad (8)$$

$$DOF = 2z_R = \frac{\lambda}{2\pi}\left(\frac{N}{NA}\right)^2 \quad (9)$$

As an example, suppose A is 1 micrometer, N is 1,000, and NA is 0.75. In this example, the DOF calculated according to equation (9) is $(8/(9\pi)) \times 10^6$ micrometers.

Returning to the description of FIG. 1, the radiation 105 having the illumination pattern 125 may be passed through a first aperture 142 such that the radiation 105 illuminates the target volume of the sample 150. Within the target volume on the sample 150, a sample including one or more objects to be imaged may be illuminated by the radiation 105. Each of the objects may generate a signal 155 in response to being illuminated by the radiation 105, and the signals 155 may be directed through a second aperture 144 towards one or more photodetectors 160. In some embodiments, each of the signals 155 may be generated based on the illumination pattern 125 shone on the target volume of the sample 150 and properties or characteristics of the object being illuminated. By leveraging the illumination pattern 125 modeled according to Equation (1), a precisely known modulation pattern may be applied to the sample 150, and the time-varying illumination pattern 125 may be matched or correlated with the time-varying fluorescent emissions of signals 155 produced in the sample 150. In some embodiments, the photodetector(s) 160 and/or other components of the microscopy system 100 may be coupled to a computing system 170 that in some embodiments may be part of the microscopy system 100. The computing system 170 may perform the matching, correlating, or other processing of, e.g., the output of the photodetector(s) 160 and/or three-dimensional localization of objects in the target volume of the sample 150 based thereon. In general, the computing system 170 may include one or more processors to perform or control performance of one or more of the operations described herein.

Figure 3B:
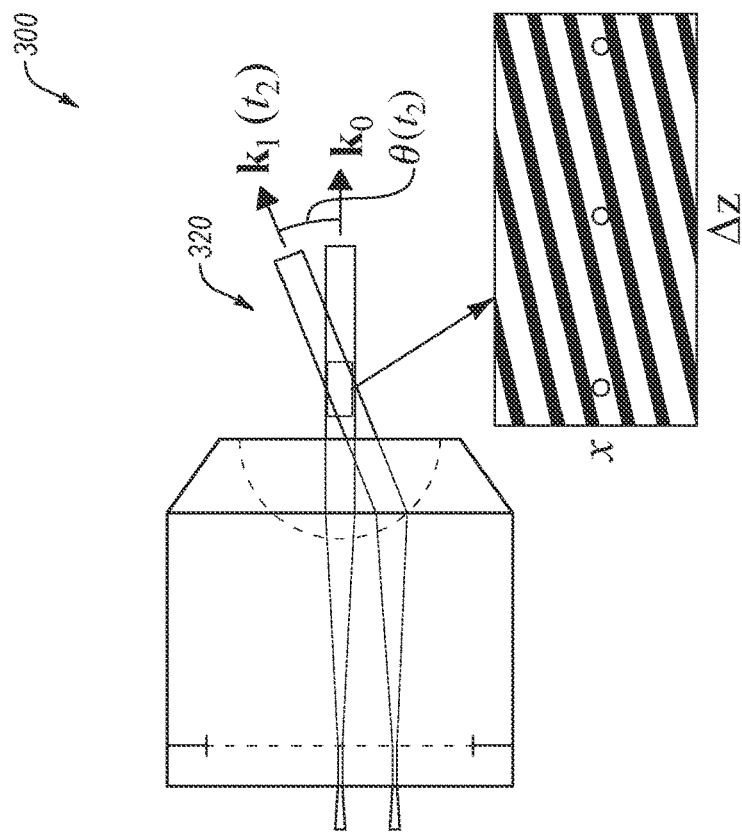
FIG. 3B illustrates a second illumination pattern generated at a second time point.
Figure 3A:
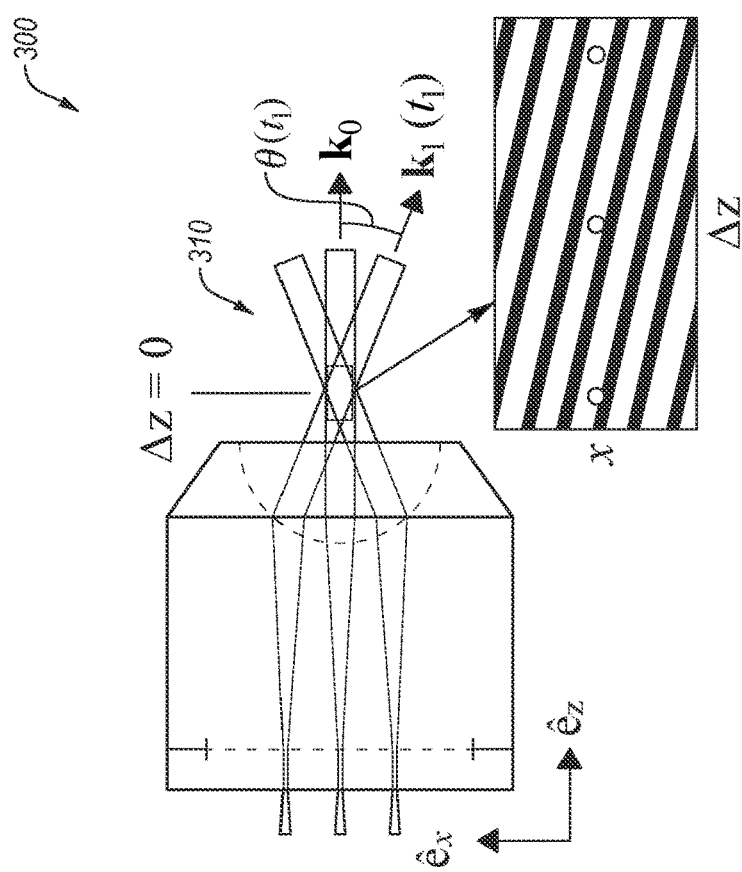
FIG. 3A illustrates a first illumination pattern generated at a first time point.

FIGS. 3A-3D illustrate examples of spatiotemporally modulated illumination intensities output by a microscopy system 300 via the partial pupil illumination process and corresponding emission intensity patterns and photocurrent signal according to at least one embodiment of the present disclosure. For example, FIG. 3A illustrates a first illumination pattern 310 generated at a first time point (i.e., where a spatial filter is positioned and angled at a first orientation), and FIG. 3B illustrates a second illumination pattern 320 generated at a second time point (i.e., where the spatial filter is positioned and angled at a second orientation). As illustrated, a first crossing angle, $\theta(t_1)$, at the first time point, $t_1$, and a second crossing angle, $\theta(t_2)$, at the second time point, $t_2$, between the crossing radiation beams may be different because at least one of the radiation beams (e.g., $k_1(t_1)$ at the first time point versus $k_1(t_2)$ at the second time point) may be directed in different directions. There may be many beam crossing angles in some embodiments.

Figure 3D:
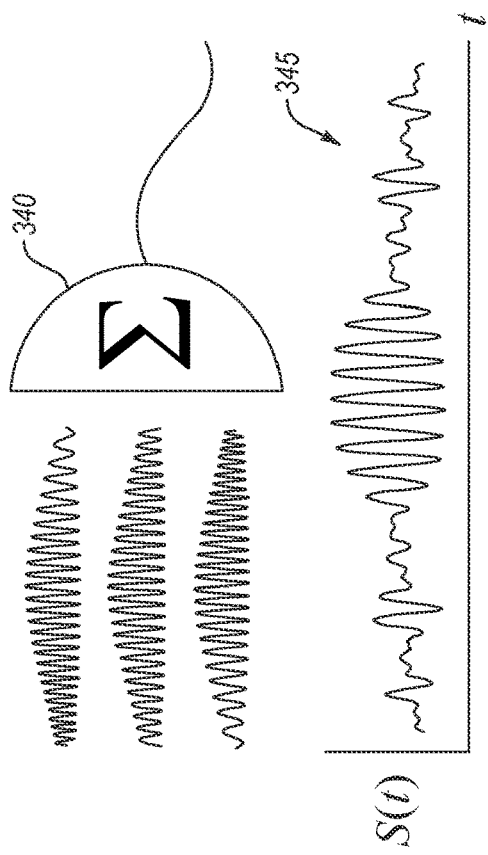
FIG. 3D illustrates a sum of the temporal illumination intensity patterns and a photocurrent signal that contains information identifying positions of the fluorophores based on the summation of the temporal illumination intensity patterns.
Figure 3C:
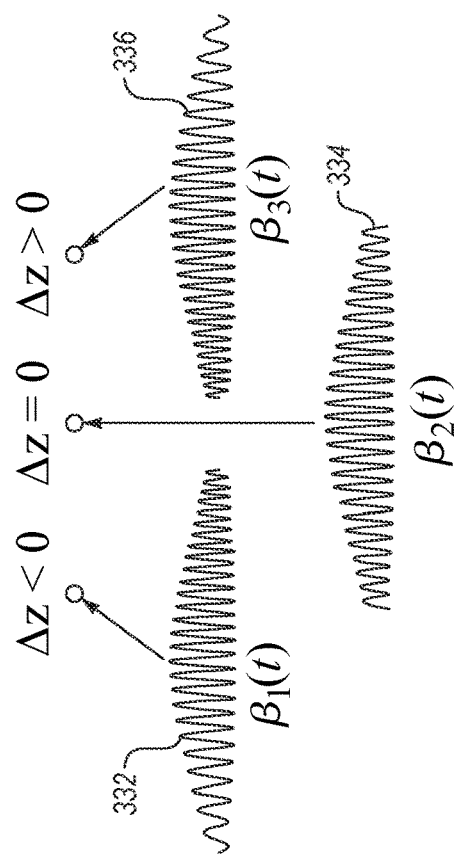
FIG. 3C illustrates examples of temporal illumination intensity patterns emitted by axially separated fluorophores.

Radiation having the first illumination pattern 310, the second illumination pattern 320, and any other illumination patterns may be used to illuminate an object. Light emitted by the object in response to being illuminated by the radiation may include temporal illumination intensity patterns that correspond to the illumination patterns of the radiation at the location of the object. FIG. 3C illustrates examples of temporal illumination intensity patterns emitted by axially separated fluorophores. A first temporal illumination intensity pattern 332, $\beta_1(t)$, may represent an emission intensity pattern located at a negative z-coordinate (e.g., $\Delta z<0$). A second temporal illumination intensity pattern 334, $\beta_2(t)$, may represent an emission intensity pattern located along the z-axis (e.g., $\Delta z=0$), and a third temporal illumination intensity pattern 336, $\beta_3(t)$, may represent an emission intensity pattern located at a positive z-coordinate (e.g., $\Delta z>0$). As shown in FIG. 3D, one or more photodetectors 340 may sum the temporal illumination intensity patterns 332, 334, 336 to generate one or more photocurrent signals 345 that contain information identifying positions of the fluorophores or other object(s) in the sample (based on their induced optical signals, e.g., fluorescence, absorption, or coherent linear or nonlinear scattering signals) that generated the temporal illumination intensity patterns 332, 334, 336. In some embodiments, temporal phenomena associated with the fluorophores or other object(s), such as photobleaching and/or blinking, may be observed based on the photocurrent signal(s) 345.

With combined reference to FIGS. 1 and 3A-3D, the photodetector(s) 160 may be configured to collect the signals 155 at each spatial point in the target volume such that a location of each of the objects may be estimated, e.g., by the computing system 170, based on the collected signals 155, or more particularly, based on a photocurrent signal output by each of the photodetector(s) 160 that is representative of the collected signals 155, and the known modulation pattern that is associated with generation of the signals 155. As an example, the photocurrent signal output by the photodetector(s) 160 may include the photocurrent signal(s) 345. The signals 155 generated by the objects may be collected by the photodetector(s) 160 from each spatial point included in the target volume at which the objects are located in a forward or a backward direction. The photodetector(s) 160 may collect light signals that correspond to the illumination pattern 125 from spatial points at which no objects are located in the target volume. In some embodiments, estimating the locations of fluorophores or other objects based on the signals 155 (or more particularly, the photocurrent signal output by the photodetector(s) 160) by the computing system 170 may be achieved using a least-squares error (LSE), a maximum likelihood estimation (MLE) optimization strategy, and/or other optimization approach(es). A modeled photocurrent signal for a single example fluorophore of infinitesimal extent may be computed using a Dirac-$\delta$ distribution, $S_\delta(t; \theta)$, in which $\theta=\{a_p, x_p, z_p\}$ is a parameter vector, $a_p$ is a brightness of the fluorophore, and $(x_p, z_p)$ is a location of the fluorophore. The parameter vector $\theta$ may be estimated by minimizing an appropriate function using, for example, the Nelder-mead simplex algorithm, or other estimation algorithm. Using a LSE approach, a $L_2$-norm of the difference between the measured signal 155 and the Dirac-$\delta$ distribution is minimized, and for a MLE approach, a negative log-likelihood function is minimized such that an illumination temporal pattern that is matched to the target object is used to estimate the location of the target object.

In some embodiments, aberrations associated with the objects being imaged on the sample 150 and/or with the microscopy system 100 itself may be identified and corrected in a post-processing step. Because spatial phase differences between two or more illumination beams are encoded in the illumination pattern 125, characteristics relating to spatial phase disruptions (i.e., aberrations), such as pupil phases, systematic misalignment of the microscopy system 100, and/or specimen aberrations on the sample 150 may inherently be included in the illumination pattern 125. Some aberrations may be corrected before any signals 155 are collected from the sample 150, such as adjustment of a correction collar of the objective lens or other aberrations related to the microscopy system 100. However, specimen aberrations may or may not be known before imaging of the objects included on the sample 150. In these and other embodiments, post-processing in the CHIRPT process may include extraction of an aberration phase in a local environment of each fluorophore and adding the extracted aberration phases to the illumination pattern 125. Based on the updated CHIRPT illumination pattern, the locations of the objects may be re-estimated such that the specimen aberrations are accounted for.

In some embodiments, deep learning or other machine learning methods may be implemented, e.g., by the computing system 170, to form initial estimates of locations of multiple objects. The deep learning methods may facilitate handling large numbers of fluorophores or other objects simultaneously. While forming an initial estimate of a single isolated fluorophore or other object may be relatively simple, providing initial estimates of the locations of multiple fluorophores or other objects simultaneously may be difficult due to interference between various fluorophores or other objects caused by holographic-like behavior of the microscopy system 100. In these and other embodiments, implementing a deep learning method, such as a generative adversarial network, to make these initial location estimates and seed locations for an iterative location estimation approach may improve the accuracy and/or efficiency of simultaneous object location estimations.

Modifications, additions, or omissions may be made to the microscopy system 100 without departing from the scope of the present disclosure. For example, the designations of different elements in the manner described is meant to help explain concepts described herein and is not limiting. For instance, in some embodiments, the lens 110, modulation mask(s) 120, spatial filter(s) 130, first aperture 142, sample 150, second aperture 144, photodetector(s) 160, and computing system 170 are delineated in the specific manner described to help with explaining concepts described herein but such delineation is not meant to be limiting. Further, the microscopy system 100 may include any number of other elements or may be implemented within other systems or contexts than those described.

Figure 4:
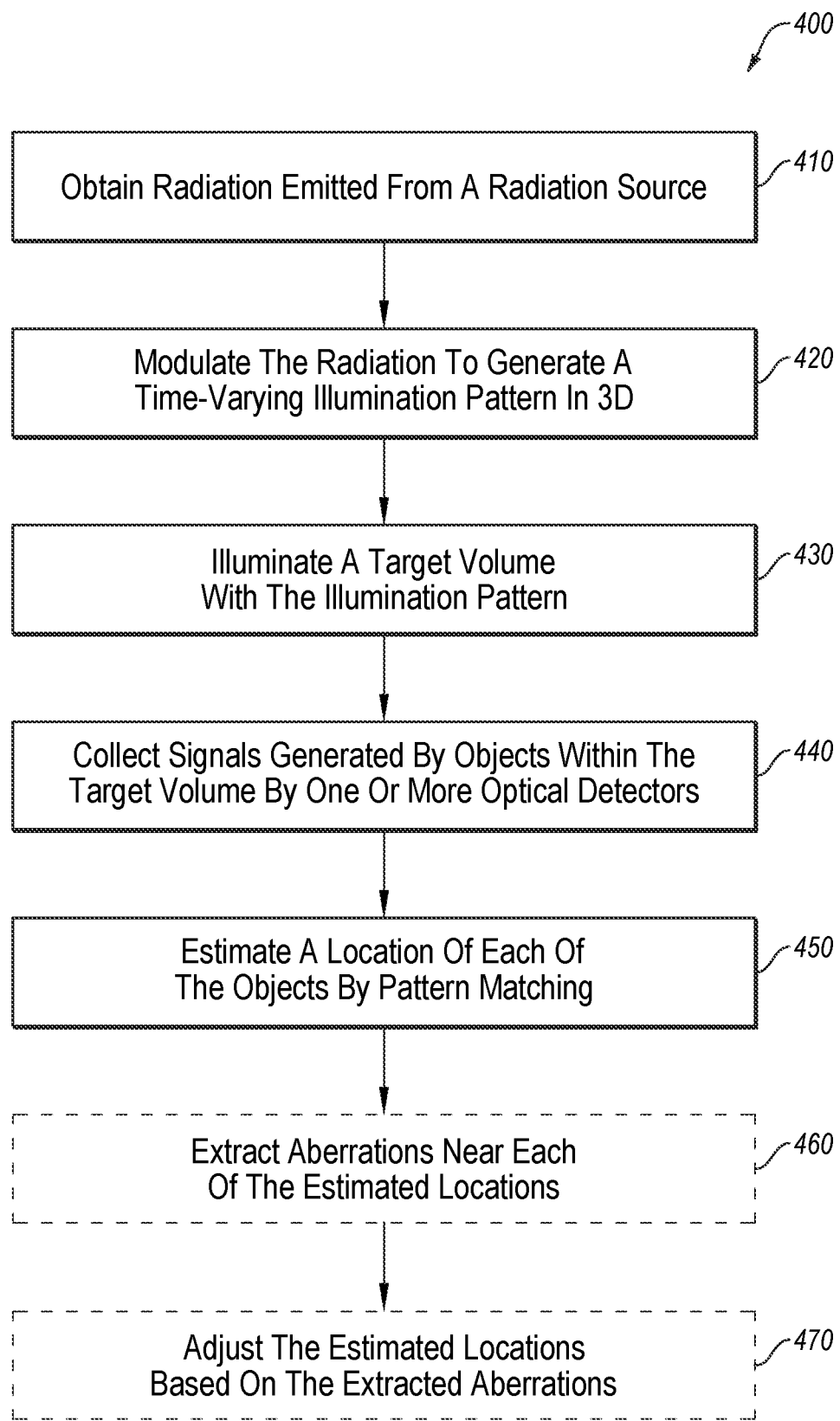
FIG. 4 is a flowchart of an example method of imaging and localizing molecules using a CHIRPT process according to at least one embodiment of the present disclosure.

FIG. 4 is a flowchart of an example method 400 of imaging and localizing molecules using a three-dimensional imaging and/or localization of one or more sample objects using large quasi-plane wave illumination process according to at least one embodiment of the present disclosure. The method 400 may be performed by any suitable system, apparatus, or device. For example, the lens 110, the modulation mask(s) 120, the spatial filter(s) 130, the first aperture 142, the sample 150, the second aperture 144, the photodetector(s) 160, and/or the computing system 170 may perform or control performance of one or more operations associated with the method 400. Although illustrated with discrete blocks, the steps and operations associated with one or more of the blocks of the method 400 may be divided into additional blocks, combined into fewer blocks, or eliminated, depending on the particular implementation.

The method 400 may begin at block 410, where radiation emitted from a radiation source is obtained. As described in relation to FIG. 1, the radiation source may emit one or more beams of radiation that includes electromagnetic waves of various wavelengths, such as infrared radiation, visible light, and/or ultraviolet radiation. The emitted radiation may be directed towards a modulation mask, such as the modulation mask(s) 120 of FIG. 1.

At block 420, the radiation may be modulated to generate a time-varying illumination pattern in three dimensions. Modulation of the radiation and generation of the time-varying illumination pattern may be facilitated by directing the radiation through the modulation mask(s), which may have a known modulation pattern etched, printed, inscribed, or otherwise provided on or by the modulation mask(s). The modulation pattern of the modulation mask(s) may selectively obstruct portions of the radiation that change over time to generate the time-varying illumination pattern.

At block 430, a target volume may be illuminated by the time-varying illumination pattern. In some embodiments, the target volume may include a volume that includes one or more objects and/or the target volume may be included on a sample (e.g., the sample 150 of FIG. 1). The objects within the target volume may generate signals in response to being illuminated by the time-varying illumination pattern.

At block 440, the signals generated by the objects in the target volume may be collected by one or more optical detectors. In some embodiments, the signals generated by the objects within the target volume in response to the time-varying illumination pattern may be collected by single-element detection sensors, such as the photodetector(s) 160 described in relation to FIG. 1. In these and other embodiments, the signals may include electro-luminescence, chemo-luminescence, absorption spectra, or spectral scattering emitted by the objects illuminated by the radiation including the time-varying illumination pattern.

At block 450, a location of each of the objects within the target volume may be estimated as described in relation to FIGS. 1 and 3A-3D.

Optionally (as indicated by the dashed box in FIG. 4) at block 460, aberrations near each of the estimated locations may be identified. In some embodiments, the aberrations may include optical aberrations associated with the microscopy system used to image the objects. Additionally or alternatively, the aberrations may include specimen-based aberrations. In these and other embodiments, the aberrations relating to the microscopy system may be removed by adjusting one or more aspects of the microscopy system, while the specimen aberrations may be removed in a post-processing step as described elsewhere herein.

Optionally (as indicated by the dashed box in FIG. 4) at block 470, the estimated locations may be adjusted based on the identified aberrations as described elsewhere herein.

Modifications, additions, or omissions may be made to the method 400 without departing from the scope of the disclosure. For example, the designations of different elements in the manner described is meant to help explain concepts described herein and is not limiting. Further, the method 400 may include any number of other elements or may be implemented within other systems or contexts than those described.

Figure 5:
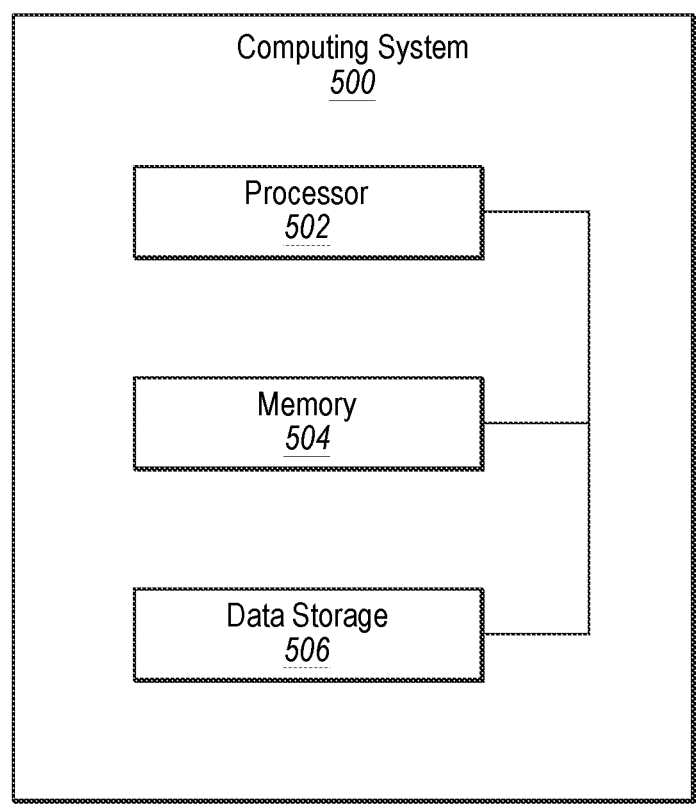
FIG. 5 illustrates a block diagram of an example computing system that may be used to perform or direct performance of one or more operations described according to at least one implementation of the present disclosure.

FIG. 5 illustrates a block diagram of an example computing system 500 that may be used to perform or direct performance of one or more operations described according to at least one implementation of the present disclosure. The computing system 500 may include, be included in, or correspond to the computing system 170 of FIG. 1. The computing system 500 may include a processor 502, a memory 504, and a data storage 506. The processor 602, the memory 504, and the data storage 506 may be communicatively coupled.

In general, the processor 502 may include any suitable special-purpose or general-purpose computer, computing entity, or processing device including various computer hardware or software modules and may be configured to execute instructions stored on any applicable computer-readable storage media. For example, the processor 502 may include a microprocessor, a microcontroller, a digital signal processor (DSP), an application-specific integrated circuit (ASIC), a Field-Programmable Gate Array (FPGA), or any other digital or analog circuitry configured to interpret and/or to execute computer-executable instructions and/or to process data. Although illustrated as a single processor, the processor 502 may include any number of processors configured to, individually or collectively, perform or direct performance of any number of operations described in the present disclosure.

In some implementations, the processor 502 may be configured to interpret and/or execute computer-executable instructions and/or process data stored in the memory 504, the data storage 506, or the memory 504 and the data storage 506. In some implementations, the processor 502 may fetch computer-executable instructions from the data storage 506 and load the computer-executable instructions in the memory 504. After the computer-executable instructions are loaded into memory 504, the processor 502 may execute the computer-executable instructions.

The memory 504 and the data storage 506 may include computer-readable storage media for carrying or having computer-executable instructions or data structures stored thereon. Such computer-readable storage media may include any available media that may be accessed by a general-purpose or special-purpose computer, such as the processor 502. By way of example, and not limitation, such computer-readable storage media may include tangible or non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 502 to perform or control performance of a certain operation or group of operations.

Some portions of the detailed description refer to different modules or components configured to perform operations. One or more of the modules or components may include code and routines configured to enable a computing system to perform or control performance of one or more of the operations described therewith. Additionally or alternatively, one or more of the modules or components may be implemented using hardware including any number of processors, microprocessors (e.g., to perform or control performance of one or more operations), DSPs, FPGAs, ASICs or any suitable combination of two or more thereof. Alternatively or additionally, one or more of the modules or components may be implemented using a combination of hardware and software. In the present disclosure, operations described as being performed by a particular module or component may include operations that the particular module or component may direct a corresponding system (e.g., a corresponding computing system) to perform. Further, the delineating between the different modules or components is to facilitate explanation of concepts described in the present disclosure and is not limiting. Further, one or more of the modules or components may be configured to perform more, fewer, and/or different operations than those described such that the modules or components may be combined or delineated differently than as described.

Some portions of the detailed description are presented in terms of algorithms and symbolic representations of operations within a computer. These algorithmic descriptions and symbolic representations are the means used by those skilled in the data processing arts to convey the essence of their innovations to others skilled in the art. An algorithm is a series of configured operations leading to a desired end state or result. In example implementations, the operations carried out require physical manipulations of tangible quantities for achieving a tangible result.

Unless specifically stated otherwise, as apparent from the discussion, it is appreciated that throughout the description, discussions utilizing terms such as detecting, determining, analyzing, identifying, scanning or the like, can include the actions and processes of a computer system or other information processing device (such as the computing systems 170, 500) that manipulates and transforms data represented as physical (electronic) quantities within the computer system's registers and memories into other data similarly represented as physical quantities within the computer system's memories or registers or other information storage, transmission or display devices.

Example implementations may also relate to an apparatus for performing the operations herein. This apparatus may be specially constructed for the required purposes, or it may include one or more general-purpose computers selectively activated or reconfigured by one or more computer programs. Such computer programs may be stored in a computer readable medium, such as a computer-readable storage medium or a computer-readable signal medium. Computer-executable instructions may include, for example, instructions and data which cause a general-purpose computer, special-purpose computer, or special-purpose processing device (e.g., one or more processors) to perform or control performance of a certain function or group of functions.

Unless specific arrangements described herein are mutually exclusive with one another, the various implementations described herein can be combined in whole or in part to enhance system functionality and/or to produce complementary functions. Likewise, aspects of the implementations may be implemented in standalone arrangements. Thus, the above description has been given by way of example only and modification in detail may be made within the scope of the present invention.

Terms used in the present disclosure and especially in the appended claims (e.g., bodies of the appended claims) are generally intended as "open terms" (e.g., the term "including" should be interpreted as "including, but not limited to.").

With respect to the use of substantially any plural or singular terms herein, those having skill in the art can translate from the plural to the singular or from the singular to the plural as is appropriate to the context or application. The various singular/plural permutations may be expressly set forth herein for sake of clarity. A reference to an element in the singular is not intended to mean "one and only one" unless specifically stated, but rather "one or more." Moreover, nothing disclosed herein is intended to be dedicated to the public regardless of whether such disclosure is explicitly recited in the above description.

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is expressly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc.

Further, any disjunctive word or phrase preceding two or more alternative terms, whether in the description, claims, or drawings, should be understood to contemplate the possibilities of including one of the terms, either of the terms, or both of the terms. For example, the phrase "A or B" should be understood to include the possibilities of "A" or "B" or "A and B."

The present invention may be embodied in other specific forms without departing from its spirit or essential characteristics. The described implementations are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method, comprising:
   obtaining radiation emitted from a radiation source;
   modulating the radiation with a time-varying modulation to generate a time-varying illumination pattern with a known modulation, wherein the illumination pattern includes a time-varying intensity for each of a plurality of spatial locations;
   illuminating a target volume with the illumination pattern;
   collecting signals generated by one or more objects within the target volume in response to illumination by the illumination pattern; and
   estimating a location of each of the one or more objects based on the collected signal and the known modulation,
   wherein:
      the radiation obtained from the radiation source includes two beams of radiation;
      the illumination pattern is generated based on interference between the beams of radiation; and
      the time-varying intensity of the illumination pattern is determined based on a background intensity, a relative amplitude of one or more fringes in the illumination pattern, and a spatial phase difference between the two beams of radiation.

2. The method of claim 1, wherein the signal generated by the objects within the target volume in response to illumination by the illumination pattern includes at least one of: electro-luminescence, chemo-luminescence, absorption spectra, linear scattering, nonlinear scattering, or spectral scattering.

3. The method of claim 1, wherein the signals generated by the objects are collected from one or more spatial points included in the target volume at which the objects are located in a forward or a backward direction.

4. The method of claim 3, wherein the signal generated by the objects within the target volume includes a summation of temporal illumination intensity patterns induced in the objects in response to illuminating the target volume with the illumination pattern, the summation being received at one or more photodetectors.

5. The method of claim 4, further comprising the one or more photodetectors generating one or more photocurrent signals of the summation of the temporal illumination intensity patterns induced in the objects.

6. The method of claim 1, wherein the time-varying intensity of the illumination pattern is determined as a sum of the background intensity, $I_0(x, y, z, t)$, and a product of an envelope of illumination intensity that determines a depth of field and an imaging volume, $I_1(x, y, z, t)$, and the cosine of the spatial phase difference, $\Delta\phi(x, y, z; t)$.

7. The method of claim 1, further comprising scanning the radiation obtained from the radiation source through a spatial filter such that a range of spatial frequencies narrower than a numerical aperture of the radiation is obtained, the numerical aperture representing an entire range of spatial frequencies of the radiation.

8. A method, comprising:
   obtaining radiation emitted from a radiation source;
   modulating the radiation with a time-varying modulation to generate a time-varying illumination pattern with a known modulation, wherein the illumination pattern includes a time-varying intensity for each of a plurality of spatial locations;
   illuminating a target volume with the illumination pattern;
   collecting signals generated by one or more objects within the target volume in response to illumination by the illumination pattern;
   estimating a location of each of the one or more objects based on the collected signal and the known modulation; and
   scanning the radiation obtained from the radiation source through a spatial filter such that a range of spatial frequencies narrower than a numerical aperture of the radiation is obtained, the numerical aperture representing an entire range of spatial frequencies of the radiation, wherein spatial frequencies along an entirety of the numerical aperture are serially scanned through the spatial filter over a period of time.

9. The method of claim 1, further comprising:
   extracting aberrations near each of the estimated locations of the objects; and
   adjusting the estimated locations of the objects based on the extracted aberrations.

10. A microscopy system, comprising:
    a radiation source configured to emit radiation;
    one or more modulation masks positioned to receive radiation from the radiation source and configured to modulate the radiation with a time-varying modulation to generate a time-varying illumination pattern with a known modulation, wherein the illumination pattern includes a time-varying intensity for each of a plurality of spatial locations;

a sample that includes one or more objects in a target volume on the sample and positioned to receive the time-varying illumination pattern;

one or more photodetectors positioned and configured to collect signals generated by the objects within the target volume in response to illumination by the illumination pattern;

a computing system coupled to the one or more photodetectors and configured to estimate a location of each of the objects based on the collected signal and the known modulation; and a spatial filter positioned between the one or more modulation masks and the sample, wherein:

the radiation emitted from the radiation source is scanned through the spatial filter such that a range of spatial frequencies narrower than a numerical aperture of the radiation is obtained, the numerical aperture representing an entire range of spatial frequencies of the radiation; and spatial frequencies along an entirety of the numerical aperture are serially scanned through the spatial filter over a period of time.

11. The microscopy system of claim 10, wherein the signal generated by the objects within the target volume in response to illumination by the illumination pattern includes at least one of: electro-luminescence, chemo-luminescence, absorption spectra, linear scattering, nonlinear scattering, or spectral scattering.

12. The microscopy system of claim 10, wherein the signals generated by the objects are collected from one or more spatial points included in the target volume at which the objects are located in a forward or a backward direction.

13. The microscopy system of claim 12, wherein the signal generated by the objects within the target volume includes a summation of temporal illumination intensity patterns induced in the objects in response to illuminating the target volume with the illumination pattern.

14. The microscopy system of claim 13, wherein the one or more photodetectors are further configured to generate one or more photocurrent signals of the summation of the temporal illumination intensity patterns induced in the objects.

15. A microscopy system, comprising:

a radiation source configured to emit radiation;

one or more modulation masks positioned to receive radiation from the radiation source and configured to modulate the radiation with a time-varying modulation to generate a time-varying illumination pattern with a known modulation, wherein the illumination pattern includes a time-varying intensity for each of a plurality of spatial locations;

a sample that includes one or more objects in a target volume on the sample and positioned to receive the time-varying illumination pattern;

one or more photodetectors positioned and configured to collect signals generated by the objects within the target volume in response to illumination by the illumination pattern; and a computing system coupled to the one or more photodetectors and configured to estimate a location of each of the objects based on the collected signal and the known modulation, wherein:

the radiation emitted from the radiation source includes two beams of radiation;

the illumination pattern is generated based on interference between the two beams of radiation; and the time-varying intensity of the illumination pattern is determined based on a background intensity, a relative amplitude of one or more fringes in the illumination pattern, and a spatial phase difference between the two beams of radiation.

16. The microscopy system of claim 15, wherein the time-varying intensity of the illumination pattern is determined as a sum of the background intensity, $I_0(x, y, z, t)$, and a product of an envelope of illumination intensity that determines a depth of field and an imaging volume, $I_1(x, y, z, t)$, and the cosine of the spatial phase difference, $\Delta\phi(x, y, z; t)$.

17. The microscopy system of claim 10, wherein estimating the location of each of the objects based on the collected signal and the known modulation further comprises:

extracting aberrations near each of the estimated locations of the objects; and adjusting the estimated locations of the objects based on the extracted aberrations.

* * * * *

UNITED STATES PATENT AND TRADEMARK OFFICE
CERTIFICATE OF CORRECTION

| | |
|---|---|
| PATENT NO. | : 12,253,662 B2 |
| APPLICATION NO. | : 17/648923 |
| DATED | : March 18, 2025 |
| INVENTOR(S) | : Randy A. Bartels and Jeffrey J. Field |

Page 1 of 1

It is certified that error appears in the above-identified patent and that said Letters Patent is hereby corrected as shown below:

In the Specification

In Column 6, Line 18, replace "other illumination beams" with --second illumination beam--.

In Column 6, Line 34, replace "1,000)." with --1,000.--.

In Column 10, Line 61, replace "processor 602," with --processor 502,--.

In Column 11, Line 65, replace "delineating" with --delineation--.

In Column 12, Line 26, replace "transmission or" with --transmission, or--.

Signed and Sealed this
Twenty-ninth Day of April, 2025

Coke Morgan Stewart
*Acting Director of the United States Patent and Trademark Office*